US00PP33276P2

(12) United States Plant Patent
Hansen

(10) Patent No.: US PP33,276 P2
(45) Date of Patent: Jul. 20, 2021

(54) ***PHLOX* PLANT NAMED 'PINK SPARKLES'**

(50) Latin Name: ***Phlox* hybrid**
Varietal Denomination: Pink Sparkles

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,294

(22) Filed: Dec. 18, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

(56) References Cited

PUBLICATIONS http://www.northbranchnursery.com/wp-content/uploads/perennial.pdf (Retrieved from the Internet on Mar. 29, 2020, 2 pages total).*

* cited by examiner

*Primary Examiner* — Susan McCormick Ewoldt

(57) ABSTRACT

A unique cultivar of Hybrid Creeping *Phlox* named 'Pink Sparkles' characterized by moderately-vigorous, dense, spreading, multi-stemmed, winter-hardy habit with short, bright-green, shiny, linear leaves. Flowering begins in mid-spring and continuing for up to six weeks in cooler weather conditions, on heavily-branched peduncles and completely cover the plant in peak season. Petals are soft baby-pink with darker eye marks and a center than lightens with maturity. The petals have a medium deep notch and the tips of the petals. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Pink Sparkles'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Dec. 1, 2019. Subsequently, the new plant was advertised in the "Walters Gardens 20-21 Catalog" by Walters Gardens, Inc. released on May 20, 2020. The claimed plant was first sold to Pleasant View Gardens/Proven Winners® on Jun. 15, 2020 by Walters Gardens, Inc., who obtained the plant and all information relating thereto, from the inventor. No plants of *Phlox* 'Pink Sparkles' have been sold in this country or anywhere in the world, nor has any enabling disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hybrid Creeping *Phlox* plant known as *Phlox* 'Pink Sparkles' and will be referred to hereafter by its cultivar name, 'Pink Sparkles', or the "new plant". The new plant was hybridized by the inventor at a wholesale perennial nursery in Zeeland, Mich. on Mar. 24, 2015 as a cross believed to be between proprietary selection of *Phlox bifida* 'Top Notch' (not patented) as the female or seed parent and

*Phlox nivalis* var. *hentzii* 'Caswell Pink Eye' (not patented) as the male or pollen parent. The new plant passed initial evaluation on the spring of 2017 and was assigned the breeder code 15-141-4 through the remaining evaluation process. 'Pink Sparkles' was first asexually propagated by stem cuttings in the greenhouses at the same nursery in Zeeland, Mich. in the summer of 2017. The unique characteristics of the new plant have been found to be reproducible and stable in successive generations of asexually propagated plants, and the resultant plants have been found to be identical to the original selection.

BRIEF SUMMARY OF THE PLANT

*Phlox* 'Pink Sparkles' is unique from all other Creeping *Phlox* known to the inventor. The nearest comparison plants known to the inventor include: the female and male parents, 'Ruby Riot' copending U.S. Plant patent application Ser. No. 16/974,227, 'Rose Quartz' copending U.S. Plant patent application Ser. No. 16/974,228, 'Majestic Magenta' U.S. Plant patent application Ser. No. 16/974,098 'Bedazzled Pink' U.S. Plant Pat. No. 32,063 and 'Rocky Road Periwinkle' U.S. Plant Pat. No. 32,325. The female parent, has soft blue flowers with deeper cleft emarginate petal apices. 'Caswell Pink Eye' has smaller flowers that are darker pink without the two distinct small bars on shorter plants. 'Ruby Riot' has a similar habit with flowers of reddish-pink and darker eyes. 'Bedazzled Pink' has a deeper pink flower color with darker center and the petals are narrower with apices that are much deeper cleft. 'Rocky Road Magenta' has a smaller habit with slower spreading growth rate and the flowers vibrant magenta-purple flowers with small dark-purple eye.

*Phlox* 'Pink Sparkles' differs from all other *Phlox* known to the inventor in the following repeatedly observed traits in combination:

1. Moderately-vigorous plants of dense spreading habit, spreading by rooting stems, producing short, clean, bright-green, shiny, linear leaves;
2. Multiple heavily-branched stems produce branched panicles;
3. Flower beginning in mid-spring and continuing for up to six weeks, in cool conditions, completely covering plant at peak flowering;
4. Flowers of soft baby-pink with darker eye bars and lighter center;
5. Petals have medium deep notches at the tip of the petals;
6. Plant is able to withstand dry conditions once established.

BRIEF DESCRIPTION OF THE DRAWINGS

The photographs of the new plant demonstrate the unique traits of *Phlox* 'Pink Sparkles' and the overall appearance of the plant at two-years-old growing in a full-sun trial garden in Zeeland, Mich. The colors in the drawings are as accurate as reasonably possible with color reproductions. Variation in ambient light spectrum, source and direction may cause the appearance of minor variation in color.

DETAILED BOTANICAL DESCRIPTION

Figure 1:
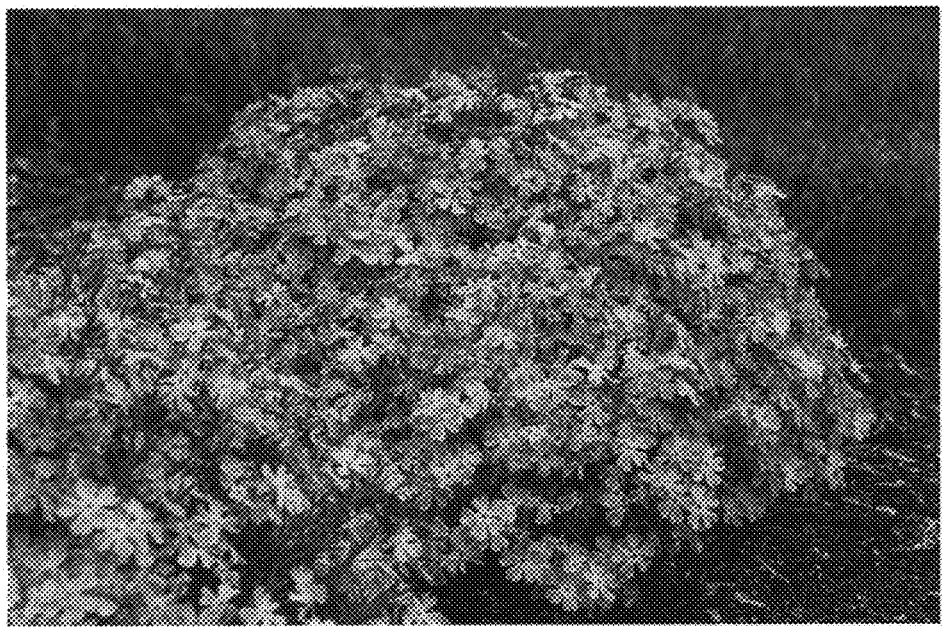
FIG. 1 shows a landscape habit view of the new plant in peak flower.
Figure 2:
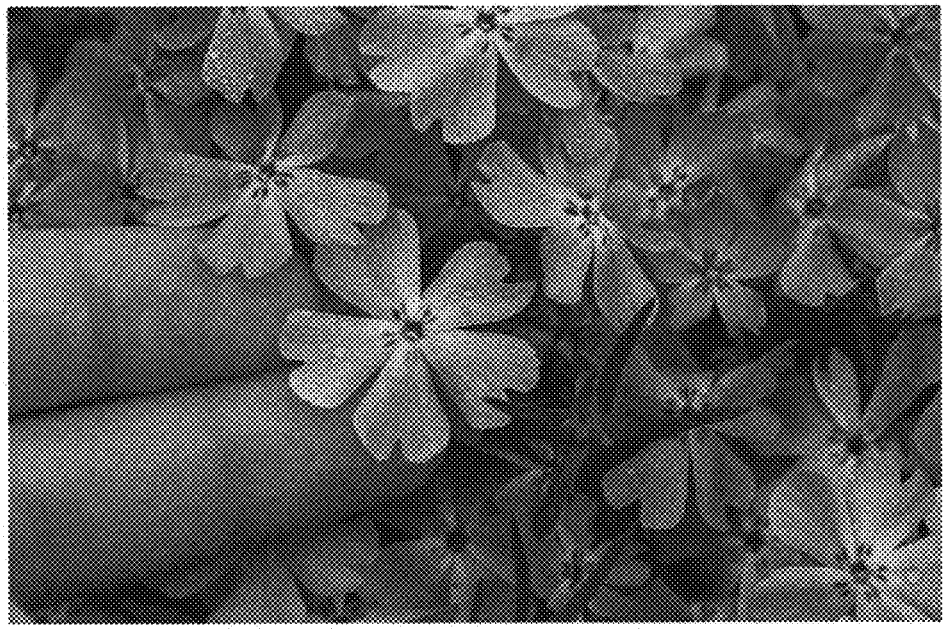
FIG. 2 shows a close-up of the flowers.

The following descriptions and color references are based on the 2015 edition of The Royal Horticultural Society Colour Chart except where common dictionary terms are used. *Phlox* 'Pink Sparkles' has not been observed under all possible environments. The phenotype may vary slightly with different growing environments such as temperature, light, fertility, soil pH, moisture and maturity levels, but without any change in the genotype. The following observations and size descriptions are based on two-year-old plants in a partially shaded greenhouse or a full-sun trial garden of a wholesale perennial nursery in Zeeland, Mich. with supplemental fertilizer and water as needed.

Botanical classification: *Phlox* hybrid;

Parentage: Female or seed parent is a proprietary selection of *Phlox bifida* 'Top Notch', male or pollen parent is 'Caswell Pink Eye';

Plant habit: Winter-hardy, evergreen herbaceous perennial; short, dense, producing about 40 stiff, highly-branched prostrate stems; foliage and stems to 18.0 cm tall and 50.0 cm wide; flowering to 28.0 cm tall and 56.0 cm wide;

Propagation: Stem cuttings; rooting in about 2 weeks;

Time to produce finished crop in 3.8 liter pots: About 10 to 12 weeks; vigorous;

Root: Fibrous and freely branching; color creamy white to tan depending on soil type;

Leaves: Simple; opposite; linear to subulate; apex narrowly acute to apiculate; base truncate, clasping; margin ciliolate; glabrous and lustrous both adaxial and abaxial; to about 26.0 mm long by about 3.5 mm wide and 0.3 mm thick at base, average about 22.5 mm long and 2.5 mm wide and 0.3 mm thick at base;

Leaf color: Adaxial expanding between RHS 136A and RHS 137A and mature adaxial nearest RHS NN137A, abaxial expanding between RHS 136A and RHS 137A and mature abaxial nearest RHS 137A; developing portions of strong blush nearest RHS 187B on both adaxial and abaxial with cold weather in late fall;

Foliage fragrance: None detected;

Veins: Pinnate; not conspicuous adaxial and abaxial;

Vein color: Adaxial midrib and veins same color as surrounding leaf; abaxial midrib nearest RHS 146B and veins same as surrounding leaf;

Petiole: Leaves sessile;

Stems: Cylindrical; flexible; wiry; prostrate; puberulent when expanding; highly compound branching; to about 39.0 mm long and 3.0 mm diameter near base;

Stem color: Young expanding with portions of both nearest RHS 145C and RHS 187B, proximal nearest RHS 195A;

Nodes: About 3.0 mm apart proximally; distally about 1.0 mm apart;

Node color: Color nearest RHS 195A proximally and nearest RHS 145B or RHS 187B distally;

Inflorescence: Upright to outwardly; about 6.5 cm long and 4.7 cm wide; average of 3.5 flowers;

Flowers: Perfect; salverform; flat-faced; about 28.0 mm across face and 13.0 mm long; with fused corolla tube about 12.0 mm long and 2.5 mm diameter near face and 2.0 mm diameter at base;

Flower aspect: Upright to outwardly;

Flowering season: Beginning early spring for at least six weeks;

Flower longevity: About 5 days on plant; self-cleaning;

Flower fragrance: Lightly sweet;

Buds one to two days prior to opening: Narrowly oblanceolate, to narrowly clavate; bluntly acute apex with rounded base; petals implicate; about 20.0 mm long, 10.0 mm long in terminal bulb portion and 10.0 mm long in tube; corolla tube to 2.0 mm diameter, bulb to 5.0 mm diameter;

Bud color: Exposed petal bulb portion nearest RHS 76A; between tube and bulb nearest RHS 79A, corolla tube basal 1.0 mm nearest RHS 145C and distal tube nearest RHS 85C; calyx with ventral portions nearest RHS 137B and dorsal portions exposed to more light nearest RHS 187B;

Petals: Five; consisting of limb and basal claw fused into corolla tube; apex rounded, slightly erose and emarginate, cleft to about 3.0 mm deep; limbs imbricate only at base; limb glabrous adaxial and abaxial, tube glabrous adaxial except puberulent in basal 3.0 mm and glabrous abaxial;

Petal size: Limb about 13.0 mm long and 9.5 mm wide near apex; corolla tube about 13.0 mm long and 2.5 mm diameter at face and 2.0 mm diameter at base;

Petal color upon first opening:

*Adaxial*.—Limb between RHS 76B and RHS 75B with two bars at the base about 1.0 mm long and 0.5 mm wide nearest RHS 83B; proximal 2.0 mm of corolla tube nearest RHS 145C, distally nearest RHS 91B and in the middle blends of between RHS 148C and RHS 85C.

*Abaxial*.—Limb between RHS 76B and RHS 75B; proximal 3.0 mm of corolla tube nearest RHS 145B, remaining distal tube nearest RHS 185B with the center portion having an undertone mixture of nearest RHS N77C and RHS 146C.

Petal color upon maturity:

*Adaxial*.—Limb between RHS 75A and RHS N74D with center fading to nearest RHS NN155D and two bars nearest RHS 93C; proximal 2.0 mm of corolla tube nearest RHS 145C, distal tube portion nearest RHS 79B.

*Abaxial*.—Between RHS 76B and RHS 75B; proximal 3.0 mm of corolla tube nearest RHS 145C, distally nearest RHS 79B.

Androecium: Typically five;

*Filaments*.—Typically five, adnate to inner corolla to various heights about 6.0 mm to 9.0 mm from base; free in the distal 0.5 mm to 1.0 mm long and 0.2 mm in diameter; color nearest RHS NN155C.

*Anther*.—Five; oblong elliptic; basifixed; oblong, about 2.0 mm long by 0.7 mm wide; color nearest RHS 17B.

*Pollen*.—Nearly microscopic; color nearest RHS 23A.

Gynoecium: One pistil per flower; 9.0 mm long;

*Style*.—Cylindrical; about 6.5 mm long and 0.2 mm diameter when flower is mature; persistent after flower abscission; color nearest RHS 157D.

*Stigma*.—Trifid in proximal 1.2 mm long, about 0.2 mm diameter; color nearest RHS 8B.

*Ovary*.—Superior; conical; glabrous; lustrous; slightly acute apex and truncate base; about 1.5 mm long and 1.0 mm diameter; color nearest RHS 144A.

Calyx: Campanulate; pubescent abaxial, glabrous adaxial; about 9.0 mm long and 4.0 mm across at apex;

Sepals: Five; linear to lanceolate; narrowly acute apex, fused in basal 3.0 mm; margin entire; puberulent and matte abaxial, glabrous and lustrous adaxial; individually about 9.0 mm long and 1.0 mm wide at fusion;

Sepal color: Adaxial nearest RHS 146A with moderate to strong blush of nearest RHS 187B and margins translucent to nearest RHS N155B, abaxial nearest RHS 138A with strong blush of nearest RHS 187B and margins translucent to nearest RHS N155B;

Peduncle: Puberulent; strong, flexible; mostly upright; cylindrical; to about 2.0 mm diameter at base and 5.5 cm long;

Peduncle color: Low light or ventrally nearest RHS 145B; high light or dorsally nearest RHS 146C with strong blush solid nearest RHS 187B;

Pedicle: Cylindrical; puberulent; flexible; upright to outwardly; variable lengths from about 6.0 mm to 4.0 mm long and 0.7 mm diameter;

Pedicle color: Variable depending on light exposure; with low light or ventrally nearest RHS 146C; high light or dorsally nearest RHS 187B;

Fruit and seeds: Not observed;

Hardiness and culture: The new plant grows best with full sun, light moisture and excellent drainage; hardy to at least from USDA zone 4 through 8.

Disease and pest resistance: *Phlox* 'Pink Sparkles' demonstrates excellent powdery mildew resistance under conditions that would normally show symptoms.

I claim:

1. A new and distinct cultivar of a Hybrid Creeping *Phlox, Phlox* plant named 'Pink Sparkles', as herein described and illustrated.

* * * * *